United States Patent [19]
Botta

[11] 3,972,890
[45] Aug. 3, 1976

[54] PROCESS FOR PREPARING A 2(ω-AMINOALKYL)-1,3-HETEROCYCLIC COMPOUNDS

[75] Inventor: Artur Botta, Krefeld-Bockum, Germany

[73] Assignee: Bayer Aktiengesellschaft, Leverkusen, Germany

[22] Filed: Apr. 15, 1974

[21] Appl. No.: 461,209

[30] Foreign Application Priority Data
Apr. 26, 1973 Germany............................ 2321054

[52] U.S. Cl...................... 260/304 R; 260/256.4 Q; 260/256.4 H; 260/306.7 R; 260/307 D; 260/307 F; 260/309.2; 260/309.6
[51] Int. Cl.²............... C07D 235/06; C07D 263/56; C07D 277/64
[58] Field of Search............ 260/307 D, 309.2, 304, 260/304 C

[56] References Cited
UNITED STATES PATENTS
2,453,234  11/1948  Koch............................ 260/239.3 A
2,985,661  5/1961  Hein et al. ........................ 260/304

OTHER PUBLICATIONS
B.A.S.F. German Pat. Nos. 824,439 and 824,440, in Chem. Abstracts, 47:1730–1731, (1953).

Primary Examiner—Richard J. Gallagher
Attorney, Agent, or Firm—Burgess, Dinklage & Sprung

[57] ABSTRACT

2-(ω-aminoalkyl)-1,3-heterocyclic compounds are prepared by reacting a compound selected from the group of a diamine, an aminohydroxy and an aminothiol compound, said compound having the formula:

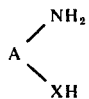

wherein

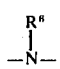

A is a bivalent chain of 2 or 3 carbon atoms, which can also be part of a bivalent, optionally substituted aliphatic, cycloaliphatic, araliphatic or aromatic radical, and
X is oxygen, sulphur or the group

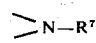

wherein
R⁷ is as defined herein with a lactam having the formula

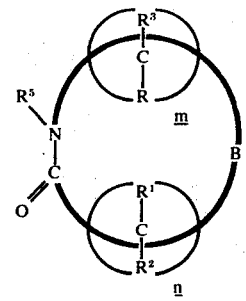

wherein
B is selected from the group of a single bond, oxygen, sulphur, the group

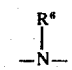

wherein
R⁶ is as defined herein, and arylene,
R¹, R², R³ and R⁴, which may be the same or different, are selected from the group of hydrogen, halogen, nitro and optionally substituted aliphatic, cycloaliphatic, araliphatic and aromatic,
R⁵, R⁶ and R⁷, which may be the same or different, are selected from the group of hydrogen and optionally substituted aliphatic, cycloaliphatic, araliphatic and aromatic, and
n and m, which may be the same or different, are intergers of from 1 to 14, with the proviso that the sum of n and m does not exceed 15, at a temperature of from 100° to 300°C in the presence of at least a catalytic quantity of an acid and/or an acid catalyst.

7 Claims, No Drawings

PROCESS FOR PREPARING A 2(ω-AMINOALKYL)-1,3-HETEROCYCLIC COMPOUNDS

BACKGROUND

This invention relates to a process for the production of 5- or 6-membered heterocyclic compounds corresponding to the general formula (I):

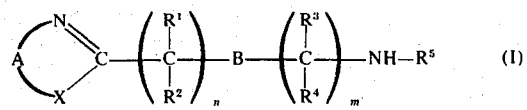

in which
A represents a bivalent chain of 2 or 3 carbon atoms which can also be part of a bivalent, optionally substituted aliphatic, cycloaliphatic, araliphatic or aromatic radical,
B represents a single bond, oxygen, sulphur or the group

and/or arylene radicals,
X represents oxygen, sulfur or the group

$R^1$, $R^2$, $R^3$, and $R^4$ are the same or different and represent hydrogen, halogen, the nitro group, an optionally substituted aliphatic, cycloaliphatic, araliphatic or aromatic radical, $R^5$, $R^6$ and $R^7$ are the same or different and represent hydrogen or an optionally substituted aliphatic, cycloaliphatic, araliphatic or aromatic radical, and $n$ and $m$ are the same or different and represent an integer from 1 to 14
The sum of $n$ and $m$ not exceeding 15.

A number of compounds of this kind are already known, being in particular derivatives of the above general formula in which X is sulphur or a substituted amino group and in which the carbon chain defined by $n$ is generally short, i.e. generally containing only 1 or 2 carbon atoms.

In general, compounds of this kind are prepared by condensing o-diamines or o-aminothiols either with ω-amino acids, in which the amino group is protected or unprotected while the carboxyl group is present either as such or in the form of its nitrile or acid chloride, or with halogen or unsaturated carboxylic acids, in which case the amino group is introduced by aminolysis of the halogen alkyl group, optionally by the Gabriel synthesis, or by the addition of ammonia or amine with existing double bonds.

Thus, 2-(ω-aminoalkyl)-benzimidazoles can be obtained for example in accordance with German Pat. No. 1,131,688 and British patent No. 1,023,792, 2-(aminoethyl)-thiazolines in accordance with Japanese Pat. No. 22,389 (1966) and Chem. Pharm. Bull. (Tokyo) 13, 180–8 (1965), and 2-(aminomethyl)- and 2-(aminoethyl)-benzthiazole in accordance with Z.obsc. Chim. 32, 3703–7 (1962) and 34, 1926–30 (1964).

In addition, compounds of formula I can be obtained in accordance with German Offenlegungsschrift No. 2,110,227 by reacting 1,2- or 1,3-diamines, aminohydroxy- or aminothiol-compounds with reactive lactam derivatives, such as lactim ethers or lactim chlorides.

ω-aminocarboxylic acids are frequently obtained on an industrial scale by hydrolysing readily available lactams, however the conversion of lactams into the more reactive lactim derivatives involves a considerable outlay. The problem of directly producing heterocycles of the general formula (I) from the corresponding lactam as the starting material, without having to resort to the formation of an intermediate product, has hitherto remained unsolved.

SUMMARY

It has now been found that 2-(ω-aminoalkyl)-1,3-heterocycles can readily be obtained in a high yield by reacting diamines, aminohydroxy or aminothiol compounds corresponding to the general formula (II):

in which
A and X are defined above,
with lactams corresponding to the general formula (III):

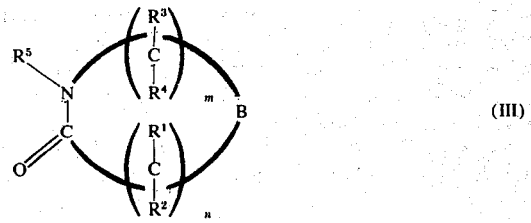

in which
B, $R^1$, $R^2$, $R^3$, $R^4$, $R^5$, $n$ and $m$ are as defined above, at a temperature of from about 100° to about 300°C in the presence of at least a catalytic quantity of acid and/or acid catalysts.

DESCRIPTION

The reaction is preferably carried out at a temperature in the range of from about 150° to about 270°C and more especially at temperatures in the range of from about 180°C to about 250°C.

The scope of meaning of the aforementioned radicals A, B, $R^1$, $R^2$, $R^3$, $R^4$, $R^5$, $R^6$ and $R^7$ is explained in more detail in the following:

The aliphatic radicals are linear or branched, optionally substituted radicals having up to 18, preferably up to 12 and more especially up to 6 carbon atoms, at least 2 carbon atoms having to be present in the case of the radical A. Preferred are saturated aliphatic hydrocarbon radicals, especially alkyl with the foregoing carbon atom contents.

The cycloaliphatic radicals are those having optionally 4 to 12 carbon atoms, in particular the cyclopentyl and the cyclohexyl radical, the radicals being optionally substituted. Preferred are saturated cycloaliphatic hydrocarbon radicals, e.g. cycloalkyl.

The aliphatic radicals are those having optionally from 7 to 15 carbon atoms, preferably those having up to 5 carbon atoms in the aliphatic portion preferably alkyl and 6 to 10 carbon atoms in the aromatic portion, in particular the benzyl, phenylpropyl and phenylbutyl radical, the radicals being optionally substituted.

The aromatic radicals are those with optionally from 6 to 14 carbon atoms, in particular the phenyl and the naphthyl radical, the radicals being optionally substituted.

The arylene radical (B) has 6 to 10 carbon atoms such as phenylene which may also be substituted.

The following are mentioned as examples of substituents for the aforementioned radicals:

Halogen (fluorine, chlorine, bromine, iodine), preferably chlorine, the nitro group, the amino group which may also be monosubstituted or disubstituted by a lower alkyl radical, the hydroxy group, alkoxy and aryloxy groups, alkylmercapto and arylmercapto groups, alkyl and arylsulphonyl groups, the alkyl and aryl radicals of the aforementioned group having the scope of meaning defined above and representing in particular $C_1$–$C_4$ alkyl or phenyl, tolyl or benzyl radical.

In the process according to the invention 1,2- or 1,3-diamines which may even be monosubstituted on one amino group can be used, the following being mentioned by way of example: ethylene diamine, 1,2-propylene diamine, 2,3-diamino butane, 3,4-diamino decane, 1,2-diamino cyclohexane, N-methylaminoethyl amine, N-phenylaminoethyl amine, diethylene triamine, N-cyclohexyl-1,2-propylene diamine, 1,3-propylene diamine, 1,3-diamino butane, 1,3-diamino-3-methyl butane, N-ethyl-1,3-propylene diamine, N-phenyl-1,3-propylene diamine, bis-(γ-aminopropyl)-amine, o-phenylene diamine, 4-methyl-, -fluoro-, -chloro-, -bromo-, -methoxy-, -phenoxy-, -nitro-, -trifluormethyl-, -ethyl-, cyclohexyl-o-phenylene diamine, 4,5-dimethyl-, -dichloro-, dibromo-, -dimethoxy-o-phenylene diamine, trichloro-o-phenylene diamine, N-methyl-, N-cyclohexyl-N-phenyl-o-phenylene diamine, N-ethyl-4- chloro-o-phenylene diamine, 1,2-diamino naphthalene, 2,3-diamino naphthalene, diamino anthracene, 9,10-diamino phenanthrene, N-methyl diamino naphthalene, N-phenyl- diamino phenanthrene, o-aminobenzylamine, o-amino-α,α-dimethylbenzylamine, o-amino-α,α-diphenylbenzylamine, o-amino-p-hydroxybenzylamine, p-amino-p-methoxybenzylamine, 1-aminomethyl-2-amino naphthalene, 2-aminomethyl-3-amino naphthalene, 1,8-diamino naphthalene, o-(N-methylamino)-benzylamine, o-aminobenzyl methylamine, o-aminomethyl diphenylamine, o-aminobenzyl benzylamine and 1-ethylamino-8 -amino naphthalene.

The following are mentioned as examples of aminothiols which can be used for the process according to the invention:
cysteamine, 2-mercapto-3-aminohexane, 1-amino-2-mercapto decane, 2-phenyl-2-mercapto ethylamine, 2-chlorphenyl-2-mercapto ethylamine, 2-p-aminophenyl-1-mercapto ethylamine, 2-mercapto cyclobutylamine, 2-mercapto cyclohexlamine, 2-mercapto cyclodecylamine, 2-mercapto -3-butyloxy-1-propyl amine, o-aminothiophenol, o,p-diaminothiophenol, p-hydroxy-o-aminothiophenol, dimethylamino-, trifluormethyl-, chloro-, bromo-, dichloro-, trichloro-, cyano-, benzoyl-, methoxy-, phenoxy-, nitro-, methyl-, isopropyl-, tert.-butyl-, cyclohexyl-, phenyl-, dimethyl- o-aminothiophenol, 1-amino- 2-mercapto naphthalene, 1-mercapto-2-amino naphthalene, 2-amino-3-mercapto naphthalene, 1-amino-2-mercapto anthracene, 9-amino-10-mercapto phenanthrene, 3-mercapto-propylamine, 1-phenyl-3-mercaptopropylamine, 2-methoxy-3-mercaptopropylamine, 3-mercapto cyclooctylamine, 3-mercaptocyclododecylamine, 3-mercapto-1-stearylamine, o-(mercaptomethyl)-aniline, o-(aminomethyl)-thiophenol, 3-chloro, 3,4-dichloro-o-(mercaptomethyl)-aniline, 3-nitro-, 3-cyano-, 3-ethoxy-o- (mercaptomethyl)-aniline, 1-(mercaptomethyl)-2-naphthylamine, 1-mercapto-8-amino naphthalene.

In addition, any aminohydroxy compounds can be used for the process according to the invention such as, for example, aminoethanol, 1,2-aminopropanol, 1,2- and 2,3-aminobutanol, 3-amino-4-hexanol, 2-amino-1-octanol, 2-amino-2-phenyl ethanol, 2-amino-1-chlorphenyl ethanol, 1-methoxy phenyl-2-amino-1-propanol, 2-amino-2-methyl-1-butanol, 2-aminocyclohexanol, 2-aminophenol, 4-chloro-2-aminophenol, 4-chloro-5-nitro-2-aminophenol, trifluormethyl-, methyl-, methoxy-, methylmercapto-, cyano-, acetyl-, benzoyl-, carbethoxy-2-aminophenol, 1-amino-2-naphthol, 2-amino-3-naphthol, 9-amino-10-hydroxy phenanthrene, 3-aminopropanol, 3-amino-1-butanol, 3-amino-1-decanol, 1-phenyl-3-hydroxy propylamine, 2-ethoxy-3-hydroxypropylamine: o-(hydroxymethyl)-aniline, o-(aminomethyl)-phenol, 3-chloro-, 3,4-dichloro-, 3trifluormethyl-, 3-methoxy-, 3-cyano-o-(hydroxymethyl)-aniline, 1-hydroxymethyl-2-naphthylamine, 1-hydroxy-8-amino naphthalene.

The following are examples of lactams of formula (III) which are unsubstituted on the nitrogen which can be used for the process according to the invention: 3-propiolactam; 3-phenyl-, 3,3-diphenyl-, 2,3-diphenyl-, 3-methyl-, 3-ethyl-, 3-benzyl-, 3,3-dimethyl-, 2,3,3-trimethyl propiolactam; 4-butyrolactam, 4,4-dimethyl butyrolactam, 5-valerolactam, 6-caprolactam, α-nitro caprolactam, the α- to ε-methyl caprolactams, the α- to ε-phenyl caprolactams, tert.-butyl caprolactam, 7-oenanthic lactam, 8-caprylic lactam, 12-lauric lactam, naphthostyril, phthalimidine, morpholone, benzmorpholone, 2-octahydroquinolone, 1H-2-oxo-4-methyl hexahydro-1,4-diazepine, 1H-2-oxo-4-isopropyl hexahydro-1,4-diazepine, 1H-2-oxo-4-benzyl hexahydro-1,4- diazepine, 1H-2-oxo-4-phenyl hexahydro-1,4-diazepine, 1H-4-methyl- 7-oxo-hexahydro-1,4-diazepine, 1H-2-oxo-5-ethyl-1,5-diazacyclo octane, 2-oxo-5,6-tetrahydroazepine.

These lactams can also be substituted on the nitrogen atom; the following representing the preferred substituents ($R^5$) of the lactim nitrogen:
methyl, ethyl, propyl, isopropyl, butyl, isobutyl, tert.-butyl, allyl, hexyl, decyl, cyclohexyl, trifluormethyl, benzyl, dimethyl benzyl, phenethyl, phenyl, fluoro-, trifluoro-, chloro-, dichloro-, trichloro-, bromo-, iodo-, nitro-, cyano-, methoxy-, phenoxy-, methylmercapto-, carbethoxy-, dimethyl amino-, methyl-, dimethyl-, tert.-butyl-, nonyl-, trifluoro methyl-, trichlormethyl-, hydroxy-phenyl; naphthyl.

Instead of using the free lactams, it is also possible to use with advantage their linear or cyclic oligomers or polymers, i.e. polymerisation waste, for the process according to the invention, for example the polyamides nylon 3, 4, 5, 6, 7, 8, 11 and 12, beginning from a polymerisation degree of 2 up to the molecular weights normally used in large-scale working.

It is, of course, also possible to use copolyamides, for example of caprolactam and butyrolactam or lauric lactam or alkyl caprolactams, mixtures of the compounds of formula (I) being formed in the same ratio in which the comonomers are used.

The following are mentioned as examples of cyclic oligomers of the aforementioned lactams which are suitable for use in the process according to the invention: cyclodicaprolactam, cyclotricaprolactam and cyclotetracaprolactam.

Any acid can be used for the process according to the invention, except for acids of the kind which are capable of taking part in undesirable secondary reactions with the reactants, for example carboxylic acids which form 1,3-heterocycles with the amino compounds of formula II. For example, it is possible to use mineral acids, such as hydrohalic acids, especially hydrochloric and hydrobromic acid, sulphuric acid, hydrogen sulphates, especially of the alkali metals, phosphoric acid, polyphosphoric acids, boric acid, tetrafluorboric acid; aliphatic and aromatic sulphonic acids such as methane sulphonic acid, hexane sulphonic acid, dodecane sulphonic acid, cyclohexane sulphonic acid, benzene sulphonic acid, toluene sulphonic acid, parachlorobenzene sulphonic acid, benzene-1,3-disulphonic acid, naphthalene sulphonic acid, naphthalene disulphonic acids; aliphatic and aromatic phosphonic acids and phosphinic acids such as cyclohexyl phosphonic acid, phenyl phosphonic acid and dimethyl phosphonic acid.

It is also possible to use Lewis acids, for example zinc(II) chloride, tin(II) chloride, boron trifluoride, aluminum chloride and titanium tetrachloride.

Suitable acid catalysts include acid-activated silicas and fullers earths such as montmorillonite, silico aluminates and silica gel, silicas in the present context being defined as finely divided materials containing silicic acid and/or aluminium oxide. Silicas and fuller earths of this kind can be activated by acid treatment as known per se (Chemie fur Labor und Betrieb, 1956, page 422; Ullmann, 3rd Edition, Vol. 9, pages 271 et seq Vol. 8, pages 801 to 804), for which purpose it is possible to use a mineral acid such as sulphuric acid, phosphoric acid, hydrochloric acid, perchloric acid or hydrofluoric acid.

It is also possible to use natural or synthetic acid ion exchangers such as zeolites or exchanger resins, exchanger resins in the present context being insoluble resins consisting of inert two-dimensionally or three-dimensionally cross-linked polymers substituted by reactive groups such as phosphoric acid, phosphonic acid, sulphuric acid or sulphonic acid groups.

Particularly suitable ion exchangers include styrene-divinyl benzene resins, crosslinked styrene resins, phenol-formaldehyde resins and benzene-formaldehyde resins, each preferably substituted by a sulphonic acid group. In particularly, it is possible to use resins of the kind containing one sulphonic acid group per 0.5 to 2 monomer units of the resin (Ullmann, 3rd Edition, Vol. 8, pages 806 to 822, especially page 816; German Pat. No. 915,267).

It is also possible to use acid-activated molecular sieves, and equally possible to use mixtures of the aforementioned acids, acid-activated silicas and fullers earths, and acid ion exchangers or any mixtures thereof.

In general, the amino compound of formula (II) is used in at least the equivalent quantity per mol of the lactam of formula (III).

However, it can also be used in an excess of up to 5 times this quantity. Preferably the excess is between 0.2 and 3 times, more particularly to between 0.3 and 0.5 times the the minimum quantity which is necessary.

The quantity of acid used in the process according to the invention can be varied within extremely wide limits. In general, the acid is used in 0.0001 to 2 times the equivalent quantity per mol of the lactam of formula (III), although even larger excesses are by no means critical.

It is possible to use both catalytic and stoichiometric quantities of acid.

In cases where only catalytic quantities of acid are used, these quantities can generally amount to between about 0.0001 and about 0.2 acid equivalents, more especially to between about 0.01 and about 0.1 acid equivalents, per mol of the lactam of formula (II) used.

In cases where the process according to the invention is carried out with a substantially stoichiometric quantity of acid, it is possible to use about 0.8 to about 2.5 acid equivalents, more especially about 1 to about 2 acid equivalents, per mol of the lactam of the general formula (III). It is of advantage to use substantially stoichiometric quantities of acids in cases where it is desired to obtain, for example, a salt or an acid addition compound of the product of the general formula (I) as the end product.

The process according to the invention can be carried out both continuously and in batches.

The process can generally be performed under any pressures; it can be performed at normal pressure, under reduced pressure or even at elevated pressure.

In general, the process according to the invention is carried out by mixing the lactam of the general formula (III) and the amino compound of the general formula (II), both of which may be used either in the form of crude products or even in solution, either in water or a solvent which is inert under the reaction conditions, and adding the selected quantity of acid. The reaction mixture is then heated, while stirring, to the reaction temperature which has been selected, optionally whilst an inert gas such as nitrogen is passed over, and kept at that temperature for a while. The water and/or the solvent eliminated during the reaction can be removed from the reaction mixture by distillation, optionally under reduced pressure.

The amino compound of formula (II) and/or the lactam of formula (III) can even be directly used in the form of a salt of the corresponding acid especially when substantially stoichiometric quantities of acid are used.

The reaction product is isolated and/or purified in the usual way on completion of the reaction by optionally fractional distillation and/or recrystallisation. In this connection, it can be of advantage, especially in cases where relatively large quantities of acid are used, to neutralise the acid before isolating the reaction product. To this end, it is of advantage, as known per se, to use in particular, aqueous solutions of the hydroxides, carbonates and hydrogen carbonates of the alkali and alkaline earth metals.

In one advantageous embodiment of the process according to the invention in which catalytic quantities of acid are used, the acid catalyst is repeatedly used for producing the same product. In this case, the reaction product and excess starting materials, if any, are removed on completion of the reaction by distillation and the starting materials used merely readded in the appropriate quantity to the distillation residue containing the catalytic quantities of acid.

The process according to the invention is explained by the following formula scheme illustrating by way of example the reaction of caprolactam with o-phenylene diamine:

$$\text{o-phenylenediamine} + \text{caprolactam} \xrightarrow[-H_2O]{acid} \text{2-(5-aminopentyl)benzimidazole}$$

The compounds which can be obtained by the process according to the invention correspond substantially to formula (I) above.

In particular, it is possible by the process according to the invention to obtain compounds which correspond to the formula (IV):

$$\text{(IV)}$$

in which;
X, $R^5$, n and m are as defined above, and
$R^8$ and $R^9$ are the same or different and represent hydrogen or an optionally substituted aliphatic, cycloaliphatic, araliphatic or aromatic radical, by reacting, as formula (II) compounds, aromatic diamines, aminophenols or aminothiophenols corresponding to the formula (V):

$$\text{(V)}$$

with lactams corresponding to the formula (VI)

$$\text{(VI)}$$

in which
X, $R^5$, $R^8$, $R^9$, m and n are as defined above.

It is possible by the process according to the invention, especially in cases where aromatic diamines or aminothiols of formula (II) are used, to obtain 2-($\omega$-aminoalkyl)-benzimidazoles corresponding to the formula $$\text{(VII)}$$

or 2-($\omega$-aminoalkyl)benzthiazoles corresponding to the formula (VIII)

$$\text{(VIII)}$$

in which;
$R^5$, $R^7$, $R^8$, $R^9$, n and m are as defined above.

In cases where the readily available ε-caprolactam and its oligomers and polymers are used as the lactam of formula (III), it is possible by the process according to the invention to obtain in particular 2-(5'-aminopentyl)- substituted 1,3-heterocycles corresponding to the formula (IX):

$$\text{(IX)}$$

in which;
A and X are as defined above. Particular reference is made here to 2-(5'-aminopentyl)-benzimidazoles, -benzthiazoles, -benzoxazoles, -imidazolines, -thiazolines and -oxazolines.

The compounds which can be obtained by the process according to the invention represent valuable intermediate products for the production of polymers and vulcanisation accelerators (cf. USSR Pat. No. 112,941); in particular they represent excellent corrosion inhibitors. Thus they are employed for example in combination with other known corrosion inhibitors, such as sodium benzoate, sodium nitrite, sodium silicate and sodium borate, in aqueous heat transfer systems as inhibitors having a synergistic effect

EXAMPLE 1 (Comparison Example)

170 g (1.5 mols) of caprolactam and 215 g (2 mols) of o-phenylene diamine are melted in a nitrogen atmosphere. No elimination of water is observed, even after stirring for several hours at 260°C.

EXAMPLE 2

170 g (1.5 mols) of caprolactam and 215 g (2 mols) of o-phenylene diamine are melted in a nitrogen atmosphere. 10 g of 85% by weight phosphoric acid (the remaining 15% by weight being water) are run into the melt with stirring, at 100°C and the heating is continued, 28 g of water distilling off over a period of 2 hours at an internal temperature of 170 to 250°C. The reaction mixture is then subjected to fractional distillation, initially in a water jet vacuum and subsequently in an oil pump vacuum. After the first distillate of excess o-phenylene diamine, 247 g (81% of the theoretical) of 2-(5'-aminopentyl)-benzimidazole are obtained in the form of a yellowish-brown solidifying in crystalline form with a boiling point of 210° to 215°C at 0.05 Torr, and a melting point of 101°C.

EXAMPLE 3

A mixture of 678 g (6 mols) of caprolactam, 865 g (8 mols) of o-phenylene diamine and 60 g of p-toluene sulphonic acid is melted in a nitrogen atmosphere, 108 g of water distilling off over a period of 6 hours at an internal temperature of 200° to 250°C. The reaction mixture is then subjected to fractional distillation under reduced pressure, giving 1003 g (82.4% of the theoretical) of 2-(5'-aminopentyl)- benzimidazole with boiling point of 210° to 215°C at 0.05 Torr, and a melting point of 101°C.

EXAMPLE 4

A mixture of 51 kg (450 mols) of caprolactam, 65 kg (600 mols) of o-phenylene diamine and 4.5 kg of p-toluene sulphonic acid is melted while stirring in a nitrogen atmosphere, and the water gradually eliminated distilled off over a period of 5 hours at a sump temperature of 150° to 250°C. The reaction mixture is then subjected to fractional distillation under reduced pressure, initially at around 100 Torr and subsequently in a high vacuum. After the first runnings of excess o-phenylene diamine distills off, and a small quantity of unreacted caprolactam, the 2-(5'-aminopentyl)-benzimidazole distills over under a pressure of 0.05 Torr and at a boiling temperature of 210° to 215°C in the form of a brownish oil which gradually solidifies in crystalline form.

The entire first runnings of distillation together with another 51 kg of caprolactam and 65 kg of o-phenylene diamine, but without p-toluene sulphonic acid as the catalyst, are added to the distillation residue containing the p-toluene sulphonic acid which is then processed in the same way as described above.

After the final distillation, another 51 kg of caprolactam and 65 kg of o-phenylene diamine, together with the first runnings of distillation are reacted in the same way and this procedure repeated three times.

A total of 306 kg of caprolactam and 390 kg of o-phenylene diamine are thus reacted in 6 runs in the presence of 4.5 kg of p-toluene sulphonic acid. The total yield of 2-(5'-aminopentyl)-benzimidazole amounts to 495 kg (90.3% of the theoretical). If 5.2 kg of 85% by weight phosphoric acid are used instead of the 4.5 kg of toluene sulphonic acid, under otherwise the same reaction conditions, 2-(5'-aminopentyl)-benzimidazole is obtained in a yield of 526 kg (96% of the theoretical).

EXAMPLE 5

339.5 g (3 mols) of caprolactam, 430 g (4 mols) of o-phenylene diamine and 30 g of 50% by weight sulphuric acid are reacted in the same way as described in Example 3, giving 510 g (83.7% of the theoretical) of 2-(5'-aminopentyl)-benzimidazole with a boiling point at 0.1 Torr of 210° to 220°C, and a melting point of 101°C.

EXAMPLE 6

A mixture of 1.7 kg (15 mols) of caprolactam, 2.16 kg (20 mols) of o-phenylene diamine and 300 g of an acid-activated montmorillonite catalyst (marketed under the name K 10 by Messrs. Südchemie, Munich), is heated with stirring to 230°–250°C in a nitrogen atmosphere, 255 g of water distilling off over a period of 12 hours beginning at an internal temperature of 170°C. On completion of the reaction, the reaction mixture is subjected to fractional distillation under reduced pressure in the same way as described in Example 3.

The distillation residue is boiled with 1500 ml of methanol, the catalyst filtered off and the filtered methanol solution concentrated under reduced pressure, after which the residue is subjected to fractional distillation, again in the same way as described above.

2-(5'-Aminopentyl)-benzimidazole with a boiling point of 210° to 220°C at 0.1 Torr, and a melting point of 101°C, is obtained in a yield of 2380 g (78% of the theoretical).

EXAMPLE 7

162 g (1.5 mols) of o-phenylene diamine, 85 g (1 mol) of pyrrolidone and 8 g of p-toluene sulphonic acid are melted, while stirring, in a nitrogen atmosphere and the water which is gradually eliminated is distilled off over a period of 5 hours at a sump temperature of 150° to 250°C. The reaction mixture is then subjected to fractional distillation under reduced pressure. 150 g (85.5% of the theoretical) of 2-(3'-aminopropyl)-benzimidazole are obtained at a pressure of 0.1 Torr and a boiling temperature of 190° to 196°C in the form of a brownish-yellow crystalline mass melting at 118°C.

EXAMPLE 8

A mixture of 56.6 g (0.5 mol) of granulated nylon-6, 91.5 g (0.75 mol) of 3,4-diaminotoluene and 5 g of p-toluene sulphonic acid is melted while stirring in a nitrogen atmosphere. The elimination of water begins at a temperature upwards of 150°C, a clear melt being formed at 200°C. The temperature is maintained at 250°C for 5 hours, during which time a total of 8 g of water distill over. In addition to the first runnings of excess 3,4-diamino toluene, subsequent fractional distillation in a high vacuum gives 92 g (84.7% of the theoretical) of 2-(5'-aminopentyl)-5-methyl benzimidazole in the form of a brownish-yellow oil with a boiling point of 216°C at 0.4 Torr.

The same yield is obtained when the nylon-6 is replaced by the same quantity by weight of cyclodicaprolactam.

EXAMPLE 9

36.5 g of hydrogen chloride gas are introduced over a period of 30 minutes into a mixture of 113 g (1 mol) of caprolactam and 125 g (1 mol) of o-aminothiophenol, followed by the introduction of another 20 g of hydrogen chloride gas over a period of 3 hours at 160°C. The melt is then stirred into a mixture of 200 g of 45% by weight sodium hydroxide and 200 g of ice, the supernatant oil separated off and the aqueous phase extracted by shaking with 200 ml of $CH_2Cl_2$. The combined organic phases are concentrated in vacuo and subsequently subjected to fractional distillation, giving 194 g (88 % of the theoretical) of 2-(5'-aminopentyl)-benzthiazole in the form of a yellowish oil with a boiling point of 131° to 133°C at 0.05 Torr.

EXAMPLE 10

250 g of hydrogen chloride gas are introduced over a period of 1.5 hours, with stirring, and heating (beginning at room temperature and terminating at 200°C), into a mixture of 339 g (3 mols) of caprolactam and 200 g (3.3 mols) of ethylene diamine. 48 g of water are then distilled off through a 20 cm Vigreux column up to a sump temperature of 270°C. The melt is allowed to cool and is stirred, while it is still pourable, into 800 g of 45% sodium hydroxide. The oil so precipitated is separated off and subjected to fractional distillation in vacuo. The yield of $\Delta^2$-2(5'-aminopentyl)-imidazoline amounts to 375 g (80.6% of the theoretical) in the form of a colourless crystalline mass with a boiling point of 120° to 125°C at 0.03 Torr and a melting point of 79° to 80°C.

EXAMPLES 11 to 20

The following compounds were prepared in the same way as described in Example 10:

| Example | Formula | Boiling point at x Torr (b.p.$_x$) Melting point (mp) |
|---|---|---|
| 11 | 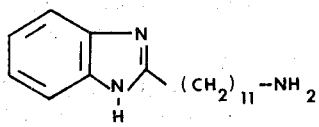 | Bp$_{0.2}$ 250°C Mp 78°C |
| 12 | 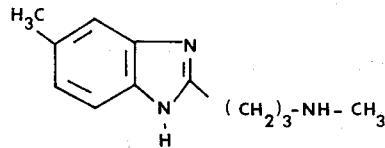 | Bp$_{0.4}$ 196–198°C Mp 126°C |
| 13 | 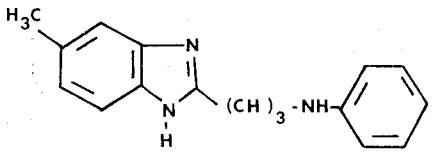 | Bp$_{0.03}$ 240°C |
| 14 | 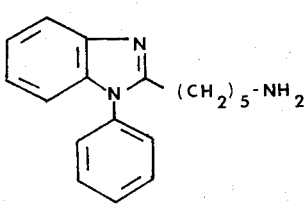 | Bp$_{0.35}$ 185–190°C |

| Example | Formula | Boiling point at x Torr (b.p.ₓ) Melting point (mp) |
|---|---|---|
| 15 | 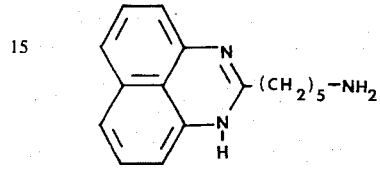 | Bp₀.₄ 235–237°C<br>Mp 194°C |
| 16 | 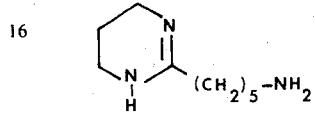 | Bp₀.₀₄ 120–123°C |
| 17 | 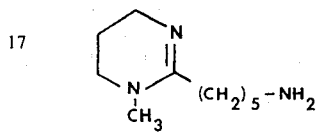 | Bp₀.₀₁ 138–140°C |
| 18 | 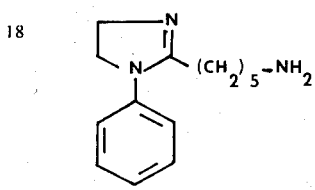 | Bp₀.₀₅ 168–170°C |
| 19 | 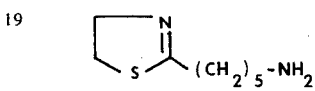 | Bp₁₂ 150–151°C |
| 20 | 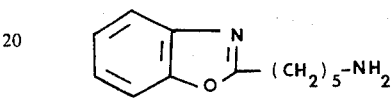 | Bp₀.₁ 125°C |
| 21 | 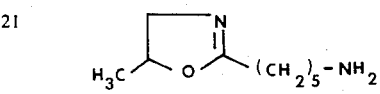 | Bp₀.₁ 78°C |

EXAMPLE 22

84.5 g (0.5 mol) of 4-tert.-butyl caprolactam, 81.1 g (0.75 mol) of o-phenylene diamine and 10 g of p-toluene sulphonic acid are melted, while stirring, in a nitrogen atmosphere. Heating is then continued, 8.5 g of water distilling off over a period of 2 hours at an internal temperature of 170° to 250°C. The reaction mixture is then subjected to fractional distillation, initially in a water jet vacuum and subsequently in an oil pump vacuum. After the first runnings of excess o-phenylene diamine, 92 g (71% of the theoretical) of 2-(5'-amino-3'-tert.-butylphentyl)-benzimidazole are obtained in the form of a light, heavily viscous oil with a boiling point of 115° to 118°C. at 0.05 Torr.

EXAMPLE 23

31.5 g (0.2 mol) of 1H-4-isopropyl-2-oxo-hexahydro-1,4-diazepine, 47.3 g (0.3 mol) of o-phenylene diamine and 15 g of 85% by weight phosphoric acid the (remaining 15% being water) are heated, with stirring, in a nitrogen atmosphere, 6.5 g of water distilling off overhead over a period of 4 hours at an internal temperature of 130° to 210°C. The melt obtained is then stirred into a mixture of 75 g of 45% by weight aqueous sodium hydroxide and 200 g of ice water, the organic phase is taken up in 300 ml of dichloroethane, dried over anhydrous sodium sulphate and the solution concentrated under reduced pressure. Subsequent fractional distillation of the residue gives 32.5 g (66% of the theoretical) of 2-[N-(3'-aminopropyl)-N-isopropyl-aminomethyl]-benzmidazole with a boiling point of 198° to 201°C at 0.2 Torr.

What is claimed is:

1. Process for preparing a 5-membered heterocycle which comprises reacting a diamine, aminohydroxy or aminothiol compound having the formula

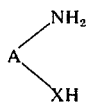

wherein

A is a bivalent aromatic radical selected from the group of o-phenylene and o-naphthylene and the foregoing substituted by halogen, nitro, amino which may also be mono- or di-substituted by lower alkyl, hydroxy, $C_{1-4}$ alkoxy, $C_{6-10}$ aryloxy, $C_{1-4}$ alkylmercapto, $C_{6-10}$ arylmercapto $C_{1-4}$ alkylsulfonyl or $C_{6-10}$ arylsulfonyl;

X is oxygen, sulfur or the group

wherein $R^7$ is as defined herein with a lactam having the formula

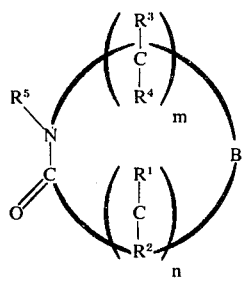

wherein

B is selected from the group of a single bond $C_{6-10}$ arylene, oxygen, sulfur and the group

wherein $R^6$ is as defined herein;

$R^1$, $R^2$, $R^3$ and $R^4$, which may be the same or different, are selected from the group of hydrogen, halogen nitro, and alkyl having up to 18 carbon atoms, cycloalkyl having 4 to 12 carbon atoms, phenylalkyl having up to 5 carbon atoms in the alkyl portion, phenyl and naphthyl and the foregoing substituted by halogen, nitro, amino which may also be mono- or di- substituted by lower alkyl, hydroxy, $C_{1-4}$alkoxy, $C_{6-10}$ aryloxy, $C_{1-4}$ alkylmercapto, $C_{6-10}$ arylmercapto, $C_{1-4}$ alkylsulfonyl or $C_{6-10}$ arylsulfonyl;

$R^5$, $R^6$ and $R^7$, which may be the same or different, are selected from the group of hydrogen and alkyl having up to 18 carbon atoms, cycloalkyl having 4 to 12 carbon atoms, phenylalkyl having up to 5 carbon atoms in the alkyl portion, phenyl and naphthyl and the foregoing substituted by halogen, nitro, amino which may also be mono- or disubstituted by lower alkyl, hydroxy, $C_{1-4}$ alkoxy, $C_{6-10}$ aryloxy, $C_{1-4}$ alkylmercapto, $C_{6-10}$ arylmercapto, $C_{1-4}$ alkylsulfonyl or $C_{6-10}$ arylsulfonyl; and n and m which may be the same or different, are integers of from 1 to 14, with the proviso that the sum of n and m does not exceed 15, at a temperature of from 100° to 300°C in the presence of an acid selected from the group of mineral acids, aliphatic and aromatic sulfonic acids, aliphatic and aromatic phosphonic acids and Lewis acids and/or an acid catalyst selected from the group of acid activated silicas and fuller earths, natural and synthetic acid ion exchangers and acid activated molecular sieves, in an amount of from 0.0001 to 2 times the equivalent quantity per mole of the lactam.

2. Process for preparing a 5-membered heterocycle in claim 1 having the formula

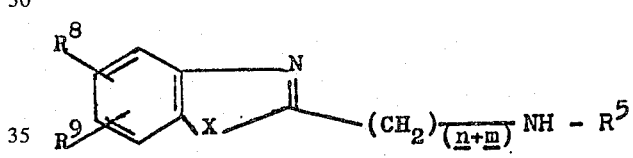

wherein

X is oxygen, sulfur or the group

$R^5$ and $R^7$, which may be the same or different, are selected from the group of hydrogen and alkyl having up to 18 carbon atoms, cycloalkyl having 4 to 12 carbon atoms, phenylalkyl having up to 5 carbon atoms in the alkyl portion, phenyl and naphthyl and the foregoing substituted by halogen, nitro, amino which may also be mono- or disubstituted by lower alkyl, hydroxy, $C_{1-4}$ alkoxy, $C_{6-10}$ aryloxy, $C_{1-4}$ alkylmercapto, $C_{6-10}$ arylmercapto $C_{1-4}$ alkylsulfonyl or $C_{6-10}$ arylsulfonyl, $R^8$ and $R^9$ which may be the same or different are selected from the group of hydrogen, halogen, nitro, amino, which may also be mono or disubstituted by lower alkyl, hydroxy, $C_{1-4}$ alkoxy, $C_{6-10}$ aryloxy, $C_{1-4}$ alkylmercapto, $C_{6-10}$ arylmercapto, $C_{1-4}$ alkylsulfonyl and $C_{6-10}$ arylsulfonyl;

(n+m) represents a number from 2 to 15, wherein compounds having the formula:

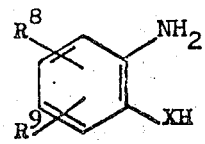

are reacted with compounds having the formula:

wherein
X, $R^5$, $R^8$, $R^9$ and ($n+m$) are as defined above.

3. Process for preparing 2-(5'-aminopentyl)-substituted 1,3-heterocycles as in claim 1 wherein the lactam is ε-captolactam.

4. Process of claim 1 wherein linear or cyclic oligomers or polymers of the lactams are used.

5. Process of claim 1 wherein the reaction is carried out at a temperature of from 180°C to 250°C 6. Process of claim 1 wherein the amino compound is used in excess of between 0.2 and 3 times the minimum quantity which is required.

7. Process of claim 1 wherein water eliminated during the reaction is removed from the reaction mixture by distillation.

\* \* \* \* \*

UNITED STATES PATENT AND TRADEMARK OFFICE
CERTIFICATE OF CORRECTION

PATENT NO. : 3,972,890
DATED : August 3, 1976
INVENTOR(S) : Artur Botta

It is certified that error appears in the above—identified patent and that said Letters Patent are hereby corrected as shown below:

In the Abstract, after "wherein", delete formula, first time it appears:

$$\begin{array}{c} R^6 \\ | \\ -N- \end{array}$$

In the Abstract, col. 2, $R^7$ formula, "R" should read $$-- R^4 --$$

Col. 5, line 29, "phosphonic" second occurence, should read

--phosphinic

Col. 9, line 24, "solidifying" should read -- <u>oil</u> solidifying --

Col. 14, line 61, "butylp[h]entyl" should read --butylpentyl--

Col. 17, line 10 "cap[t]olactam" should read -- caprolactam --.

Signed and Sealed this

Thirtieth Day of November 1976

[SEAL]

Attest:

RUTH C. MASON
*Attesting Officer*

C. MARSHALL DANN
*Commissioner of Patents and Trademarks*

UNITED STATES PATENT AND TRADEMARK OFFICE
CERTIFICATE OF CORRECTION

PATENT NO. : 3,972,890
DATED : August 3, 1976
INVENTOR(S) : Artur Botta

It is certified that error appears in the above-identified patent and that said Letters Patent are hereby corrected as shown below:

Column 4, line 29, change "3tri- to -- 3-tri- --.

Signed and Sealed this

Twenty-second Day of February 1977

[SEAL]

Attest:

RUTH C. MASON
Attesting Officer

C. MARSHALL DANN
Commissioner of Patents and Trademarks